United States Patent
Meglan et al.

(10) Patent No.: US 10,912,449 B2
(45) Date of Patent: *Feb. 9, 2021

(54) SURGICAL SYSTEM FOR DETECTING GRADUAL CHANGES IN PERFUSION

(71) Applicant: Covidien LP, Mansfield, MA (US)

(72) Inventors: Dwight Meglan, Westwood, MA (US); Meir Rosenberg, Newton, MA (US)

(73) Assignee: COVIDIEN LP, Mansfield, MA (US)

( * ) Notice: Subject to any disclaimer, the term of this patent is extended or adjusted under 35 U.S.C. 154(b) by 384 days.

This patent is subject to a terminal disclaimer.

(21) Appl. No.: 15/768,150

(22) PCT Filed: Oct. 20, 2016

(86) PCT No.: PCT/US2016/057797
§ 371 (c)(1),
(2) Date: Apr. 13, 2018

(87) PCT Pub. No.: WO2017/070275
PCT Pub. Date: Apr. 27, 2017

(65) Prior Publication Data
US 2018/0310811 A1    Nov. 1, 2018

Related U.S. Application Data

(60) Provisional application No. 62/245,526, filed on Oct. 23, 2015.

(51) Int. Cl.
*A61B 1/00* (2006.01)
*A61B 5/0402* (2006.01)
(Continued)

(52) U.S. Cl.
CPC .......... *A61B 1/00186* (2013.01); *A61B 1/005* (2013.01); *A61B 1/00009* (2013.01);
(Continued)

(58) Field of Classification Search
CPC ..... A61B 1/00186; A61B 1/07; A61B 1/0676; A61B 1/00096; A61B 90/361;
(Continued)

(56) References Cited

U.S. PATENT DOCUMENTS 7,558,618 B1    7/2009 Williams
8,239,170 B2    8/2012 Wegerich
(Continued)

OTHER PUBLICATIONS

European Office Action dated Mar. 6, 2020 corresponding to counterpart Patent Application EP 16858177.5.
(Continued)

*Primary Examiner* — Wayne H Cai

(57) ABSTRACT

The present disclosure is directed to an augmented reality surgical system. The system includes an endoscope that captures an image of the region of interest of a patient and an ECG device that records an ECG of the patient. A controller receives the image and applies at least one image processing filter to the image. The image processing filter includes a decomposition filter that decomposes the image into frequency bands. A temporal filter is applied to the frequency bands to generate temporally filtered bands. An adder adds each band frequency band to a corresponding temporally filtered band to generate augmented bands. A reconstruction filter generates an augmented image by collapsing the augmented bands. The controller also receives the ECG and processes the augmented image with the ECG to generate an ECG filtered augmented image. A display displays the ECG filtered augmented image to a user.

20 Claims, 5 Drawing Sheets

(51) Int. Cl.
| | |
|---|---|
| *A61B 1/005* | (2006.01) |
| *A61B 1/05* | (2006.01) |
| *A61B 1/06* | (2006.01) |
| *A61B 1/07* | (2006.01) |
| *A61B 5/00* | (2006.01) |
| *A61B 90/00* | (2016.01) |
| *A61B 34/35* | (2016.01) |

(52) U.S. Cl.
CPC ............ *A61B 1/00096* (2013.01); *A61B 1/05* (2013.01); *A61B 1/0669* (2013.01); *A61B 1/0676* (2013.01); *A61B 1/07* (2013.01); *A61B 5/0402* (2013.01); *A61B 5/7289* (2013.01); *A61B 90/361* (2016.02); *A61B 34/35* (2016.02); *A61B 2090/365* (2016.02)

(58) Field of Classification Search
CPC ................ A61B 5/0404; A61B 5/7289; A61B 2090/365; A61B 1/00009; A61B 1/05; A61B 1/005; A61B 1/0669; A61B 5/0402; A61B 34/35
See application file for complete search history.

(56) References Cited

U.S. PATENT DOCUMENTS

| | | |
|---|---|---|
| 8,271,071 B2 | 9/2012 | Maruccio |
| 8,696,685 B2 | 4/2014 | Gilboa |
| 2007/0055128 A1 | 3/2007 | Glossop |
| 2010/0158330 A1* | 6/2010 | Guissin ................ A61B 5/445 382/128 |
| 2013/0035581 A1 | 2/2013 | Vesto |
| 2013/0038707 A1 | 2/2013 | Cunningham et al. |
| 2014/0213849 A1 | 7/2014 | Pandey |
| 2014/0275760 A1 | 9/2014 | Lee et al. |
| 2015/0257653 A1* | 9/2015 | Hyde ................ A61B 5/0077 600/473 |
| 2017/0202633 A1 | 7/2017 | Liu |

OTHER PUBLICATIONS

International Search Report and Written Opinion of Int'l Appln. PCT/US16/057797 dated Feb. 1, 2017.

Extended European Search Report dated May 23, 2019 corresponding to counterpart Patent Application EP 16858177.5.

* cited by examiner

SURGICAL SYSTEM FOR DETECTING GRADUAL CHANGES IN PERFUSION

CROSS-REFERENCE TO RELATED APPLICATIONS

This application is a U.S. National Stage Application filed under 35 U.S.C. § 371(a) of International Patent Application Serial No. PCT/US2016/057797, filed Oct. 20, 2016, which claims the benefit of and priority to U.S. Provisional Patent Application Ser. No. 62/245,526, filed Oct. 23, 2015, the entire disclosure of which is incorporated by reference herein.

BACKGROUND

Minimally invasive surgeries have involved the use of multiple small incisions to perform a surgical procedure instead of one larger opening. The small incisions have reduced patient discomfort and improved recovery times. The small incisions have also limited the visibility of internal organs, tissue, and other matter.

Endoscopes have been inserted in one or more of the incisions to make it easier for clinicians to see internal organs, tissue, and other matter inside the body during surgery. These endoscopes have included a camera with an optical and/or digital zoom capability that is coupled to a display showing the magnified view of organs, tissue, and matter inside the body as captured by the camera. Existing endoscopes and displays, especially those used in surgical robotic systems, have had a limited ability to identify conditions or objects that are within the field of view of the camera but are not fully visible within the spectrum shown on the display. For example, existing minimally invasive and robotic surgical tools, including but not limited to endoscopes and displays, have had a limited, if any, ability to identify blood perfusion during a minimally invasive surgical procedure. In order to identify blood perfusion, many procedures involved adding taggants to the patient's blood stream.

In view thereof, there is a need for identifying a greater range of possible conditions or objects that are within the field of view of a surgical camera but are not fully visible within the spectrum shown on the display during surgery.

SUMMARY

The present disclosure relates to video imaging techniques of target surgical sites, in vivo, during a surgical procedure, for detecting gradual changes in perfusion of tissue at the target surgical site.

In an aspect of the present disclosure, an augmented reality surgical system is provided. The system includes an endoscope configured to capture an image of a region of interest of a patient and an electrocardiogram (ECG) device configured to record electrical activity of a heart of the patient. The system also includes a controller configured to receive the image and apply at least one image processing filter to the image to generate an augmented image. The image processing filter includes a decomposition filter configured to decompose the image into a plurality of frequency bands, a temporal filter that is configured to be applied to the plurality of frequency bands to generate a plurality of temporally filtered bands, an adder configured to add each band in the plurality of frequency bands to a corresponding band in the plurality of temporally filtered bands to generate a plurality of augmented bands, a reconstruction filter configured to generate an augmented image by collapsing the plurality of augmented bands, and an ECG filter configured to generate the ECG filtered augmented image based on the augmented image and the electrical activity. The ECG filtered augmented image of the patient is then displayed to a user.

The image capture device may capture a video having a plurality of image frames and the controller applies the at least one image processing filter to each image frame of the plurality of image frames.

The temporal filter isolates at least one frequency band from the plurality of frequency bands to generate the plurality of temporally filtered bands. The plurality of temporally filtered bands are amplified by an amplifier before each band in the plurality of frequency bands is added to a corresponding band in the plurality of temporally filtered bands to generate a plurality of augmented bands.

The ECG filter may generate a baseline time varying signal. The ECG filter may average the baseline time varying amplified color and remove the averaged baseline time varying amplified color from the augmented image.

In some aspects, the endoscope includes an illumination device or optical fiber light guide. The endoscope may emit light having a wavelength that is selectively absorbed or reflected by arterial blood and/or venous blood.

In another aspect of the present disclosure, a method for generating an electrocardiogram (ECG) filtered augmented image is provided. The method includes capturing at least one image using an endoscope and recording electrical activity of a heart of the patient using an ECG device. The at least one image is decomposed to generate a plurality of frequency bands. A temporal filter is applied to the plurality of frequency bands to generate a plurality of temporally filtered bands. Each band in the plurality of frequency bands is added to a corresponding band in the plurality of temporally filtered bands to generate a plurality of augmented bands. The plurality of augmented bands is collapsed to generate an augmented image. The augmented image and the electrical activity are used to generate the ECG filtered augmented image which is displayed on a display.

At least one frequency band is isolated from the plurality of frequency bands. The temporally filtered bands may be amplified before adding each band in the plurality of frequency bands to a corresponding band in the plurality of temporally filtered bands to generate a plurality of augmented bands.

A baseline time varying amplified color is generated whish may then be averaged. The averaged baseline time varying amplified color is removed from the augmented image to generate the ECG filtered augmented image.

In some aspects, light having a wavelength that is selectively absorbed or reflected by arterial blood or venous blood is emitted onto the tissue.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
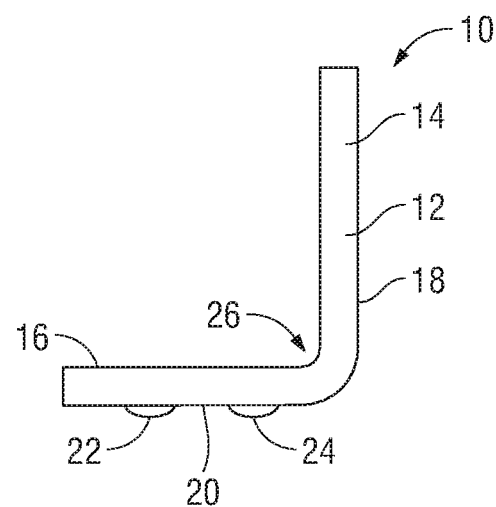
FIG. 1 is a schematic side view of an endoscope in accordance with embodiments of the present disclosure.

Image data captured from a surgical camera during a surgical procedure may be analyzed to identify additional not readily human perceivable properties of objects within the camera field of view that may not be apparent to people viewing the camera image displayed on a screen. Various image processing technologies may be applied to this image data to identify different conditions in the patient. For example, Eulerian image amplification techniques may be used to identify small wavelength or "color" changes of light in different parts of a captured image. These changes may be further analyzed to identify re-perfusion, arterial flow, and/or vessel types.

Eulerian image amplification may also be used to make motion or movement between image frames more visible to a clinician. In some instances changes in a measured intensity of predetermined wavelengths of light between different image frames may be presented to a clinician to make the clinician more aware of the motion of particular objects of interest (such as blood).

Hyper-spectral image analysis may be used to identify subtle changes in small areas within the range of view that may be invisible or otherwise difficult for the human eye to discern. These hyper-spectral image analysis techniques may be combined with Eulerian image amplification to identify a specific set of changes in these areas.

One or more of Eulerian image amplification, image algebra, hyper-spectral image analysis, and filtering technologies may be included as part of an imaging system. These technologies may enable the imaging system to provide additional information about unapparent conditions and objects within a camera's field of view and enhance surgical outcomes. This additional information may include, but is not limited to, identifying tissue perfusion, locating arteries of specific sizes (such as larger arteries), verifying an effectiveness of vessel sealing, identifying a heat signature of abnormal tissue, verifying desired object motion (such as a lack of movement in edges of dead tissue or verifying proper flow after resection), distinguishing between similar looking objects (such as between the ureter, inferior mesenteric artery, and/or surrounding blood), and detecting small leaks (such as leaks that may occur after an anastomosis).

One or more of these technologies may be included as part of an imaging system in a surgical robotic system to provide a clinician with additional information in real time about unapparent conditions and objects within an endoscope's field of view. This may enable the clinician to quickly identify, avoid, and/or correct undesirable situations and conditions during surgery. For example, a clinician may be able to verify during surgery that vessels have been properly sealed, that blood is properly flowing, that there are no air leaks after an anastomosis, and/or that diseased tissue has been removed. The clinician may then be able to correct these issues if needed during the surgery. A clinician may also be able to identify delicate or critical objects in the body that the surgical instruments should avoid contacting or handle with extra care, such as larger arteries or the ureter.

Meanwhile, an electrocardiogram (ECG) device is generally used to measure the electrical activity of a patient's heart. The electrical activity corresponds to the cyclic change of blood flow through the body. There is a consistent correlation between the electrical activity and the variation in blood flow at a target region.

The present disclosure is directed to systems and methods for providing an augmented image in real time to a clinician during a surgical procedure. The systems and methods described herein apply image processing filters to a captured image to provide an augmented or enhanced image to a clinician via a display. In some embodiments, the systems and methods permit video capture during a surgical procedure. The captured video is processed in real time or near real time and then displayed to the clinician as an augmented image. The image processing filters are applied to each frame of the captured video. Providing the augmented image or video to the clinician permits the clinician to identify and address potential adverse physiologic conditions thereby reducing the need for additional surgical procedures as well as ensuring the effectiveness of the original surgical procedure.

The embodiments described herein enable a clinician to identify and filter out the cyclical change in blood flow, i.e., resulting from the propagation of flow from the heart, in the augmented image to permit a clinician to determine if there is an abnormal change in blood perfusion. The clinician may also determine if the change in blood perfusion is within the arterial blood flow or the venous blood flow. The embodiments described herein use a concept known as ECG gating in which data is acquired in relation to the ECG identified cardiac cycle. Using ECG gating to time average the color amplification of a region of interest, permits subtle changes in tissue to be readily and immediately observed without adding taggants or making modifications to existing endoscopes. The systems described herein permit clinicians to see and understand clinically significant situations such as blood flow obstructions from clamping of tissue.

Turning to FIG. 1, an endoscope 10 according to an embodiment of the present disclosure is illustrated. An example of endoscope 10 can be found in U.S. patent application Ser. No. 14/150,443 filed on Jan. 8, 2014, the contents of which are hereby incorporated by reference. The endoscope 10 includes an elongated shaft 12 having a proximal portion 14 and a distal portion 16. In one embodiment, the elongated shaft 12 is made from shape-memory alloy (e.g. Nitinol) such that the elongate shaft 12 may have a straight or linear cylindrical configuration in a relaxed state (i.e., in the absence of externally applied forces). In the linear configuration, the distal portion 16 of the endoscope 10 is inserted into a conventional trocar sleeve or cannula (not shown), which is essentially a straight, hollow instrument that allows the endoscope 10 to be inserted into the abdominal cavity of a patient. The cannula and/or endoscope 10 may be supported on the arm of a robotic surgical system. The cannula is typical of known cannulas in the art and is made from polyvinyl chloride (PVC) or any other flexible material suitable for use in the abdominal cavity or other medical applications.

Prior to insertion of the elongated shaft 12 into the cannula and the abdominal cavity, the surgeon adjusts the elongated shaft 12 into a pre-bent configuration to obtain an optimal viewing window. The elongated shaft 12 is then returned to the original straight configuration. Once inserted into the abdominal cavity, the elongated shaft assumes the pre-bent configuration. In one embodiment, the elongated shaft 12 assumes the pre-bent configuration in response to temperature within the body cavity. In an alternate embodiment, the elongated shaft 12 responds to an electrical signal from a control unit.

With continued reference to FIG. 1, the proximal and distal portions 14, 16 of the elongated shaft 12 each have an outer surface 18, 20, respectively. The outer surface 20 of the distal portion 16 includes at least one image capturing device 22 thereon. The image capturing device 22 allows the surgeon to clearly view the inside of the abdominal cavity. Preferably, the image capturing device 22 is a low profile camera so that the image capturing device 22 does not obstruct the surgeon's tools during the procedure. At least one illumination device 24 is disposed adjacent the image capturing device 22 to illuminate the inside of the abdominal cavity and aide in viewing the internal organs with the image capturing device 22.

The image capturing device 22 and illumination device 24 can be disposed in varying configurations along the distal portion 16 of the elongated shaft 12. Based on the location of the image capturing device 22, the elongated shaft 12 is pre-bent to provide the desired location as well as optimal angle for the surgeon. This variation in the pre-bent configuration is determined by varying the length of the bent portion (i.e. the distal portion) and the angle of the bend 26. FIG. 1 illustrates the angle of the bend 26 as a generally ninety degree angle with the distal portion 16 being generally the same length as the proximal portion 14, however, it is understood that any bend angle to allow the surgeon to view the body cavity can be achieved. Further, FIG. 1 illustrates the image capturing device 22 and the illumination device 24 generally along the same longitudinal axis with the image capturing device 22 being near a distal end of the elongated shaft 12. It will be appreciated that this configuration can be altered during manufacturing based on the particular needs of the surgical procedure.

Figure 2A:
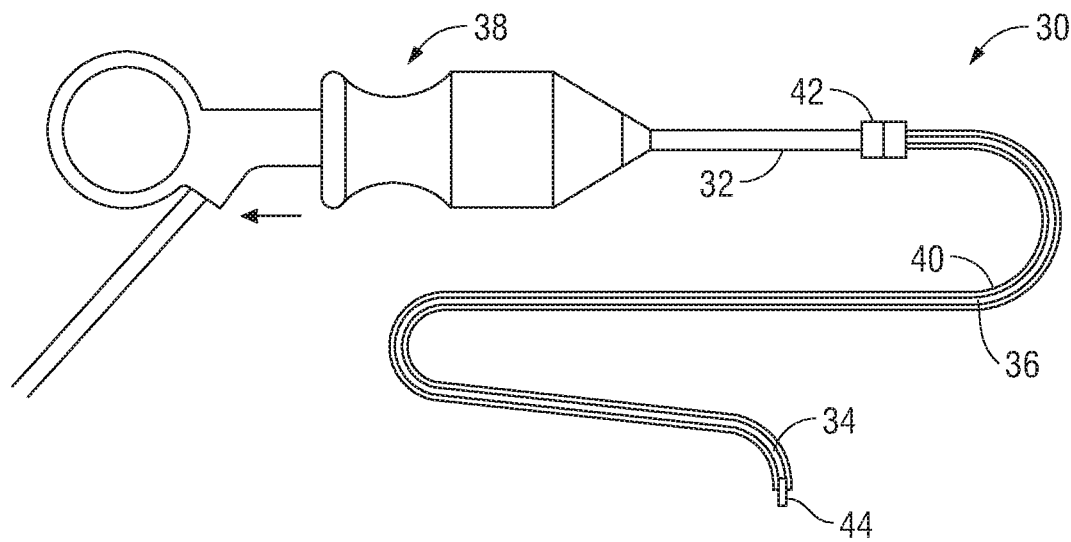
FIG. 2A is a schematic side view of a steerable endoscope in accordance with embodiments of the present disclosure.

Turning to FIG. 2A, an endoscope in accordance with another embodiment of the present disclosure is shown generally as 30. Endoscope 30 includes a locatable guide 32 which has a steerable distal tip 34, a flexible body 36 and, at its proximal end, a control handle or housing 38. Guide 32 may be inserted into a sheath 40 and may be locked in position by a locking mechanism 42 or any other connectors. A position sensor element 44 is integrated with distal tip 34 and allows monitoring of the tip position and orientation (6 degrees of freedom) relative to a reference coordinate system. An example of endoscope 30 can be found in U.S. patent application Ser. No. 12/723,577 filed on Mar. 12, 2010, the contents of which are hereby incorporated by reference.

Figure 2B:
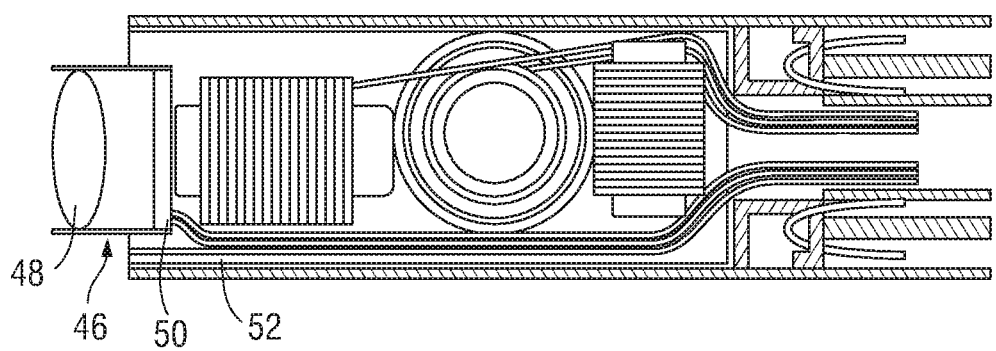
FIG. 2B is a cross sectional view of a distal end of the endoscope of FIG. 2A.

Turning now to FIG. 2B, distal tip 34 of endoscope 30 includes an image sensor 46. By way of example, image sensor 46 is shown here as an optical imaging sensor with a lens 48 positioned in front of an image sensor array 50. Illumination is provided via an optic fiber light guide 52.

The illumination device 24 of FIG. 1 and the optical fiber light guide 32 may emit specific light frequencies that may be used to illuminate a surgical site to selectively enhance the visibility or arterial and venous blood flow.

Figure 3:
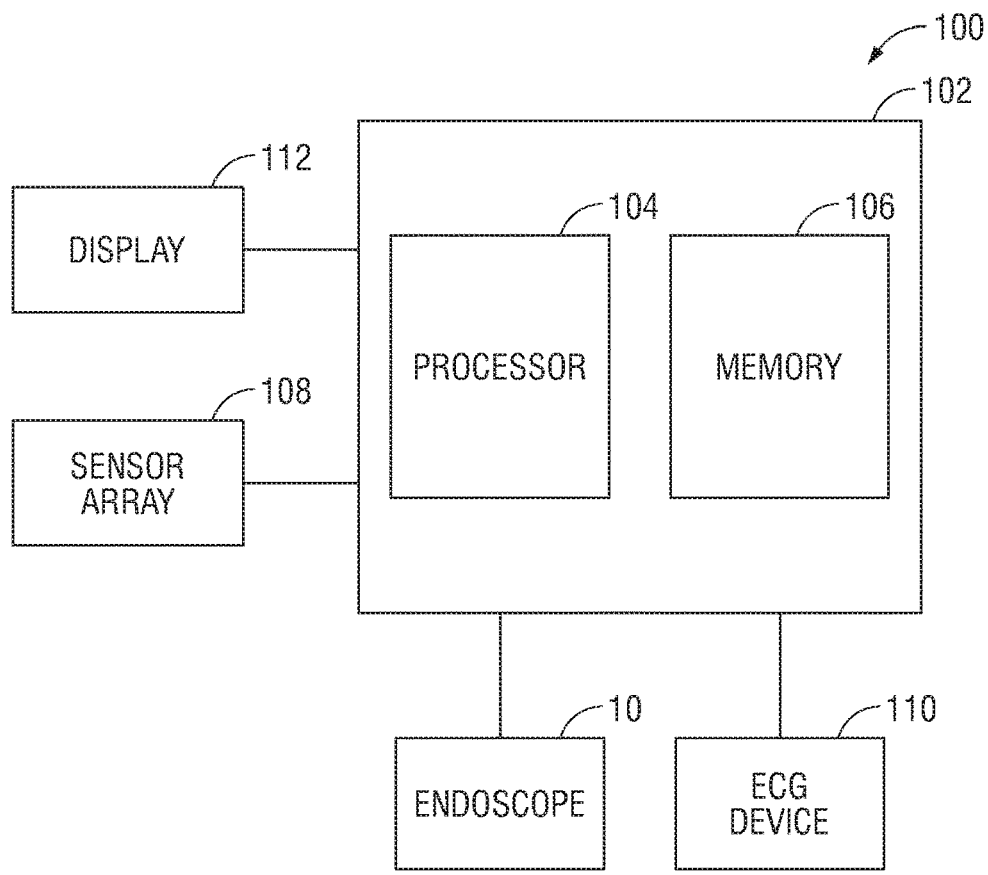
FIG. 3 is a block diagram of a system for augmenting an image or video in accordance with an embodiment of the present disclosure.

Turning to FIG. 3, a system for augmenting a surgical environment, according to embodiments of the present disclosure, is shown generally as 100. System 100 includes a controller 102 that has a processor 104 and a memory 106. The system 100 receives images from endoscope 10 or endoscope 30.

A sensor array 108 of system 100 provides information concerning the surgical environment to the controller 102. For instance, sensor array 108 includes biometric sensors capable of obtaining biometric data of a patient such as, pulse, temperature, blood pressure, blood oxygen levels, heart rhythm, etc. Sensor array 108 may also include hyper-spectral sensors to perform hyper-spectral imaging. Sensor array 108 may be incorporated in endoscope 10 or endoscope 30 or sensor array 108 may be provided as a separate standalone unit.

An ECG device 110 of system 100 provides an ECG or electrical activity signals of the heart of the patient to the controller 102. A display 112 of system 100, displays augmented images to a clinician during a surgical procedure. In some embodiments, the controller 102 may communicate with a central server (not shown) via a wireless or wired connection. The central server may store images of a patient or multiple patients that may be obtained using x-ray, a computed tomography scan, or magnetic resonance imaging.

Figure 4:
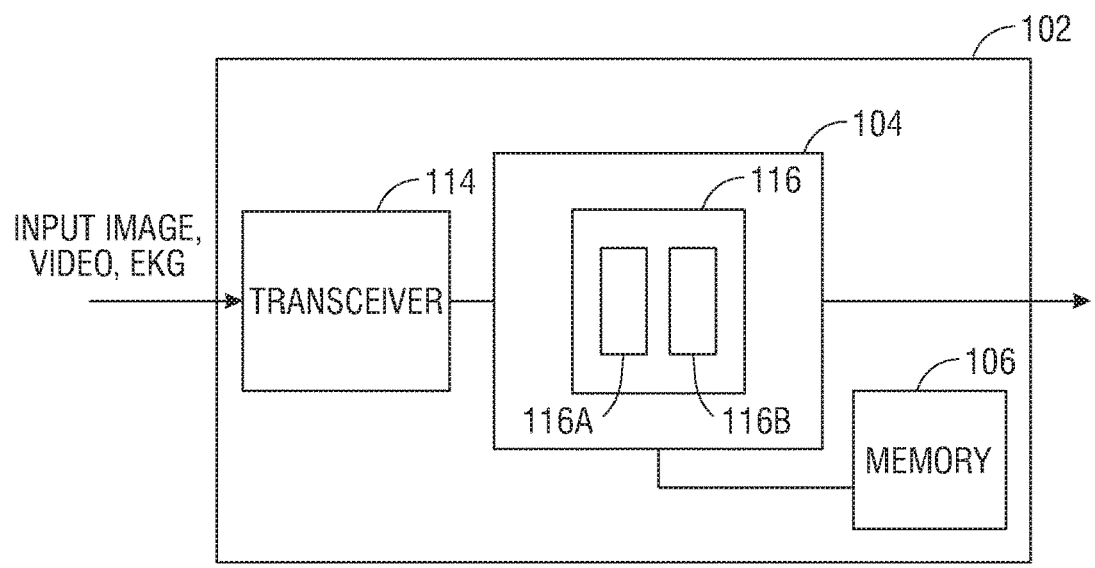
FIG. 4 is a system block diagram of a controller of FIG. 3.

FIG. 4 depicts a system block diagram of the controller 102. As shown in FIG. 4, the controller 102 includes a transceiver 114 configured to receive still frame images or video from endoscope 10, data from sensor array 110, or ECG data or signals from the ECG device 110. In some embodiments, the transceiver 114 may include an antenna to receive the still frame images, video, data, or ECG data or signals via a wireless communication protocol. The still frame images, video, data, or ECG data or signals are provided to the processor 104. The processor 104 includes an image processing filter 116 that processes the received still frame images, video, data, or ECG data or signals to generate an augmented image or video. The image processing filter 116 may be implemented using discrete components, software, or a combination thereof. The augmented image or video is provided to the display 112.

Figure 5:
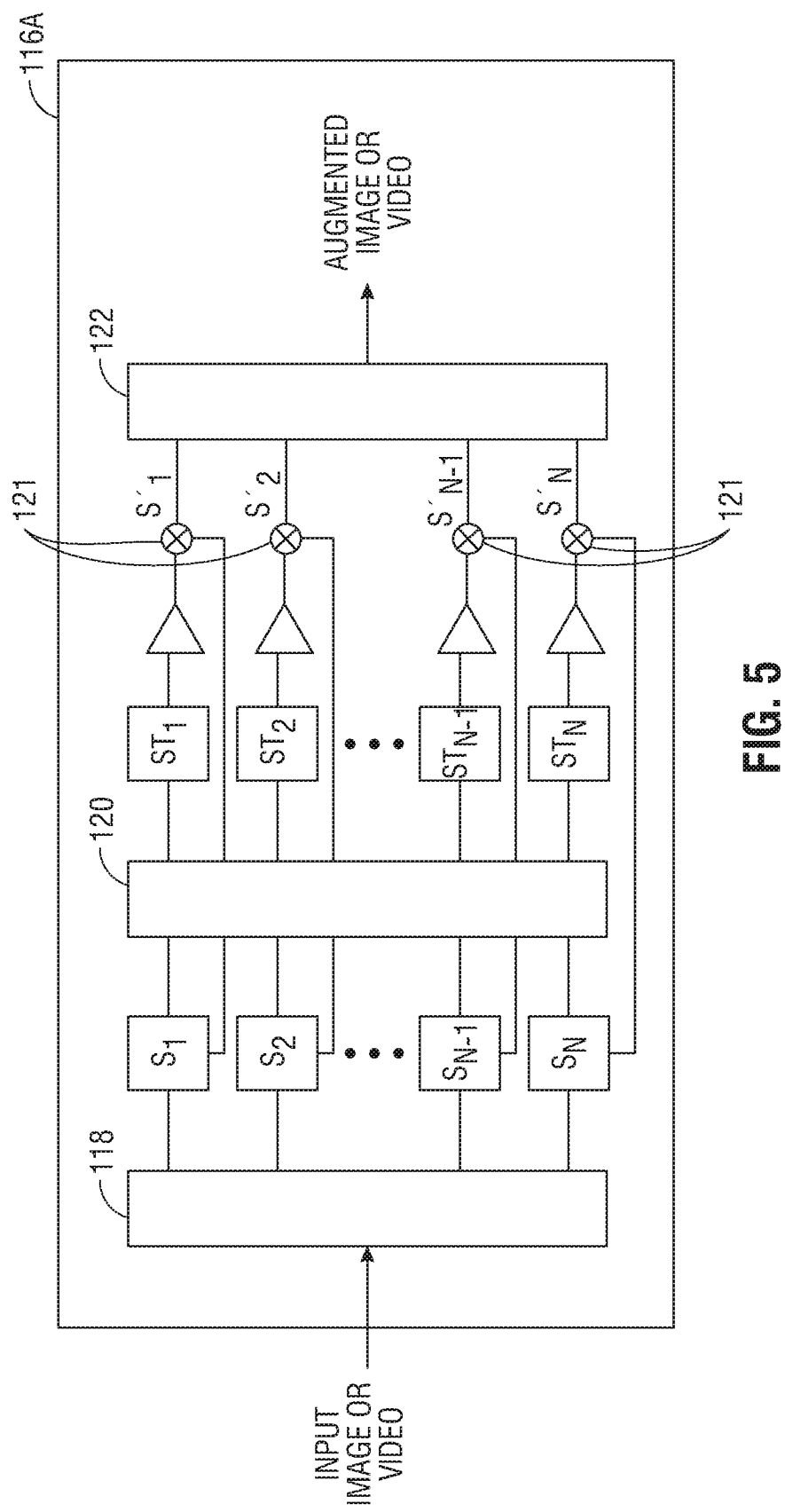
FIG. 5 is a system block diagram of a sub assembly of an image processing filter of FIG. 4.

Turning to FIG. 5, a system block diagram of an image processing filter that may be applied to video received by transceiver 114 is shown as 116A. In the image processing filter 116A, each frame of a received video is decomposed into different frequency bands $S_1$ to $S_N$ using a decomposition filter 118. The decomposition filter 118 uses an image processing technique known as a pyramid in which an image is subjected to repeated smoothing and subsampling.

After the frame is subjected to the decomposition filter 118, a temporal filter 120 is applied to all the frequency bands $S_1$ to $S_N$ to generate temporally filtered bands $ST_1$ to $ST_N$. The temporal filter 120 is a bandpass filter that is used to extract one or more desired frequency bands. For example, if the clinician knows the patient's pulse, the clinician can set the bandpass frequency of the temporal filter 120, using a user interface (not shown), to magnify the frequency band that corresponds to the patient's pulse. In other words, the bandpass filter is set to a narrow range that includes the patient's pulse and applied to all the frequency bands $S_1$ to $S_N$. Only the frequency band that corresponds to the set range of the bandpass filter will be isolated or passed through. In an embodiment, the bandpass frequency of the temporal filter 120 may be set automatically by system 100 based on the patient's pulse being measured by a pulse sensor, included in sensor array 108, and transmitted to temporal filter 120.

All of the temporally filtered bands $ST_1$ to $ST_N$ are individually amplified by an amplifier having a gain "$\alpha$".

Because the temporal filter 120 isolates or passes through a desired frequency band of bands $S_1$ to $S_N$, only the desired frequency band of bands $S_1$ to $S_N$ gets amplified. The amplified temporally filtered bands $ST_1$ to $ST_N$ are then added, by adder 121, to the original frequency bands $S_1$ to $S_N$ to generate augmented bands $S'_1$ to $S'_N$. Each frame of the video is then reconstructed using a reconstruction filter 122 by collapsing augmented bands $S'_1$ to $S'_N$ to generate an augmented frame. All the augmented frames are combined to produce the augmented video. The augmented video that is shown to the clinician includes a portion that is magnified, i.e., the portion that corresponds to the desired frequency band, to enable the clinician to easily identify such portion.

In some embodiments, instead of using an amplifier to amplify the isolated temporally filtered band, the image processing filter 116A may highlight the temporally filtered band using one or more colors before reconstructing the video. Using an enhanced color for a desired portion of the patient, e.g., a vessel or nerve, may make it easier for the clinician to identify the location of such portion.

Figure 6:
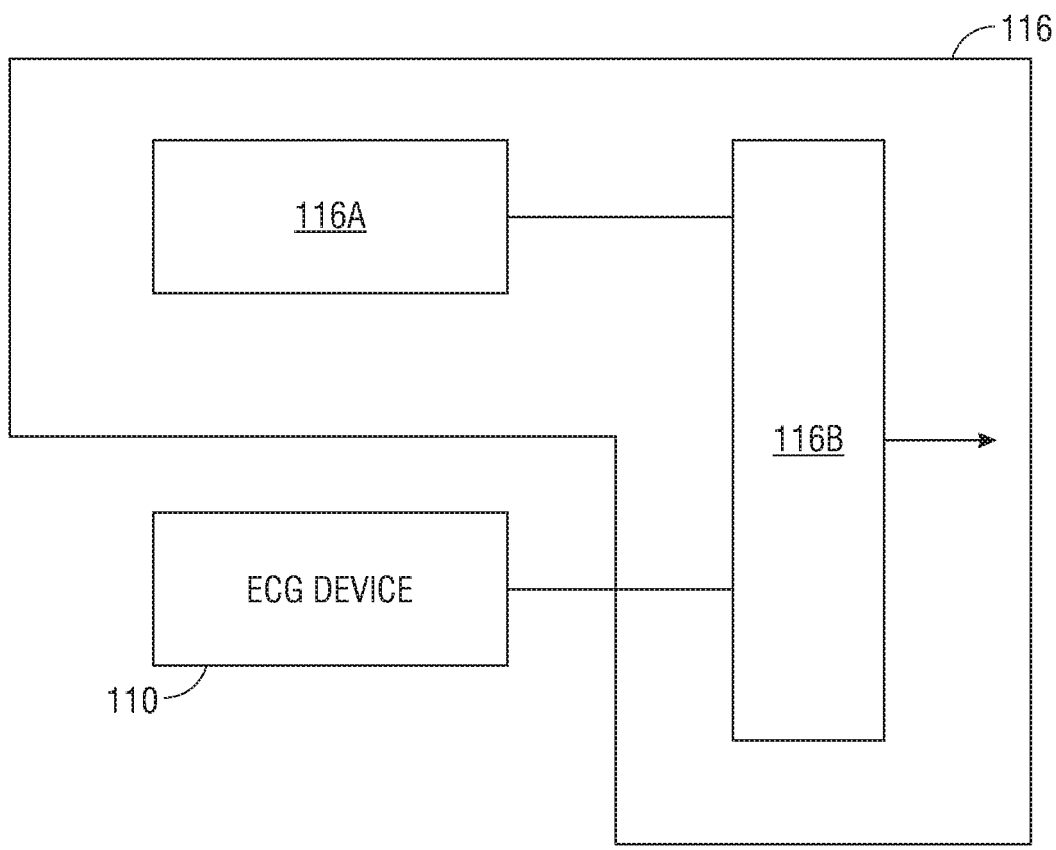
FIG. 6 is a system block diagram of the image processing filter of FIG. 4.

Turning to FIG. 6, image processing filter 116A feeds the augmented video to ECG filter 116B. ECG filter 116B also receives ECG data or signals that were obtained by ECG device 110. Because the ECG data or signals is correlated with a cyclic change in blood flow, there is a consistent offset between the ECG data or signals and variation in blood flow at the surgical site. By using the consistent offset, the ECG filter 116B may determine a baseline time varying signal using the QRS signal pattern observed in the ECG data or signals. The ECG filter 116B then averages the baseline time varying signal and removes the average signal from the augmented video to generate an ECG filtered augmented video. In the ECG filtered augmented video, only unique changes in blood flow are visible, thus permitting a surgeon to view situations in real time, e.g., cessation in blood flow from over clamping tissue using jaw like end effector.

The image processing performed by image processing filter 116 may be combined with the specific light wavelengths emitted by illumination device 24 or optical fiber light guide 52, e.g., 660 nm and 940 nm, to determine if there is an abnormal blood flow in the arterial system or the venous system. Specifically, the illumination device 24 or optical fiber light guide 52 may emit light having a wavelength that selectively is absorbed or reflected by arterial blood. The received images and the ECG data or signals are processed by the image processing filter 116 to check for abnormalities in the arterial blood flow. The same procedure would apply to venous blood except that the illumination device 24 or optical fiber light guide 52 would emit light having a wavelength that isolates venous blood.

The above-described embodiments may also be configured to work with robotic surgical systems and what is commonly referred to as "Telerobotic surgery." Such systems employ various robotic elements to assist the clinician in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include, remotely steerable systems, flexible surgical systems, remotely flexible surgical systems, remotely articulating surgical systems, wireless surgical systems, modular or selectively configurable remotely operated surgical systems, etc.

Figure 7:
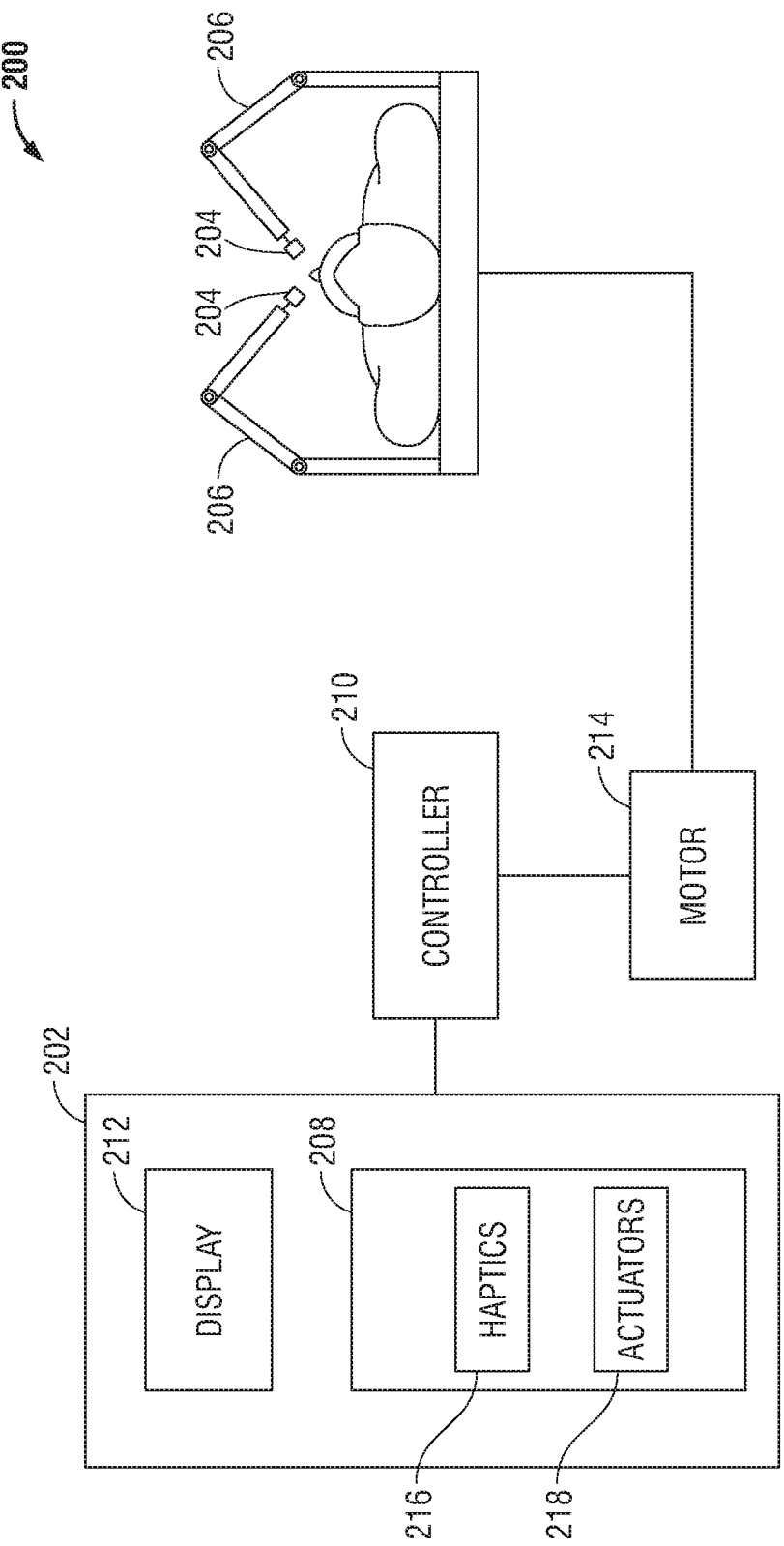
FIG. 7 is a system block diagram of a robotic surgical system in accordance with an embodiment of the present disclosure.

As shown in FIG. 7, a robotic surgical system 200 may be employed with one or more consoles 202 that are next to the operating theater or located in a remote location. In this instance, one team of clinicians or nurses may prep the patient for surgery and configure the robotic surgical system 200 with one or more instruments 204 while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

The robotic arms 206 of the surgical system 200 are typically coupled to a pair of master handles 208 by a controller 210. Controller 210 may be integrated with the console 202 or provided as a standalone device within the operating theater. The handles 206 can be moved by the clinician to produce a corresponding movement of the working ends of any type of surgical instrument 204 (e.g., probe, end effectors, graspers, knifes, scissors, etc.) attached to the robotic arms 206. For example, surgical instrument 204 may be a probe, e.g., endoscope, that includes an image capture device. The probe is inserted into a patient in order to capture an image of a region of interest inside the patient during a surgical procedure. One or more of the image processing filters 116A or 116B are applied to the captured image by the controller 210 before the image is displayed to the clinician on a display 212.

The movement of the master handles 208 may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s) 204.

During operation of the surgical system 200, the master handles 208 are operated by a clinician to produce a corresponding movement of the robotic arms 206 and/or surgical instruments 204. The master handles 208 provide a signal to the controller 208 which then provides a corresponding signal to one or more drive motors 214. The one or more drive motors 214 are coupled to the robotic arms 206 in order to move the robotic arms 206 and/or surgical instruments 204.

The master handles 208 may include various haptics 216 to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such haptics 216 provide the clinician with enhanced tactile feedback simulating actual operating conditions. The haptics 216 may include vibratory motors, electroacitve polymers, piezoelectric devices, electrostatic devices, subsonic audio wave surface actuation devices, reverse-electrovibration, or any other device capable of providing a tactile feedback to a user. The master handles 208 may also include a variety of different actuators 218 for delicate tissue manipulation or treatment further enhancing the clinician's ability to mimic actual operating conditions.

The embodiments disclosed herein are examples of the disclosure and may be embodied in various forms. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments," which may each refer to one or more of the same or different embodiments in accordance with the present disclosure. A phrase in the form "A or B" means "(A), (B), or (A and B)". A phrase in the form "at least one of A, B, or C" means "(A), (B), (C), (A and B), (A and C), (B and C), or (A, B and C)". A clinician may refers to a clinician or any medical professional, such as a doctor, nurse, technician, medical assistant, or the like) performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C#, C++, Delphi, Fortran, Java, JavaScript, Machine code, operating system command languages, Pascal, Perl, PL1, Python, scripting languages, Visual Basic, metalanguages which themselves specify programs, and all first, second, third, fourth, and fifth generation computer languages. Also included are database and other data schemas, and any other meta-languages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. For instance, any of the augmented images described herein can be combined into a single augmented image to be displayed to a clinician. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. An augmented reality surgical system comprising:
   an endoscope configured to capture an image of a region of interest of a patient;
   an electrocardiogram (ECG) device configured to record electrical activity of a heart of the patient;
   a controller configured to receive the image and apply at least one image processing filter to the image to generate an ECG filtered augmented image, the image processing filter including:
      a decomposition filter configured to decompose the image into a plurality of frequency bands;
      a temporal filter that is configured to be applied to the plurality of frequency bands to generate a plurality of temporally filtered bands;
      an adder configured to add each band in the plurality of frequency bands to a corresponding band in the plurality of temporally filtered bands to generate a plurality of augmented bands;
      a reconstruction filter configured to generate an augmented image by collapsing the plurality of augmented bands; and
      an ECG filter configured to generate the ECG filtered augmented image based on the augmented image and the electrical activity; and
   a display configured to display the ECG filtered augmented image of the patient to a user during the surgical procedure.

2. The augmented reality surgical system of claim 1, wherein the endoscope captures a video having a plurality of image frames and the controller applies the at least one image processing filter to each image frame of the plurality of image frames.

3. The augmented reality surgical system of claim 1, wherein the temporal filter includes a bandpass filter.

4. The augmented reality surgical system of claim 3, wherein a bandpass frequency of the bandpass filter is set by a clinician.

5. The augmented reality surgical system of claim 1, wherein the temporal filter isolates at least one frequency band from the plurality of frequency bands to generate the plurality of temporally filtered bands.

6. The augmented reality surgical system of claim 1, wherein the plurality of temporally filtered bands are amplified by an amplifier before each band in the plurality of frequency bands is added to the corresponding band in the plurality of temporally filtered bands to generate the plurality of augmented bands.

7. The augmented reality surgical system of claim 1, wherein the ECG filter generates a baseline time varying signal.

8. The augmented reality surgical system of claim 7, wherein the ECG filter averages the baseline time varying amplified color and removes the averaged baseline time varying amplified color from the augmented image.

9. The augmented reality surgical system of claim 1, wherein the endoscope includes an illumination device or an optical fiber light guide.

10. The augmented reality surgical system of claim 1, wherein the endoscope emits light having a wavelength that selectively is absorbed or reflected by arterial blood.

11. The augmented reality surgical system of claim 1, wherein the endoscope emits light having a wavelength that selectively is absorbed or reflected by venous blood.

12. The augmented reality surgical system of claim 1, further comprising a temperature filter configured to identify heat signatures of abnormal tissue.

13. A method for generating an electrocardiogram (ECG) filtered augmented image of a region of interest of a patient during a surgical procedure, the method comprising:
- capturing at least one image of the region of interest using an endoscope;
- recording electrical activity of a heart of the patient using an ECG device;
- decomposing the at least one image to generate a plurality of frequency bands;
- applying a temporal filter to the plurality of frequency bands to generate a plurality of temporally filtered bands;
- adding each band in the plurality of frequency bands to a corresponding band in the plurality of temporally filtered bands to generate a plurality of augmented bands;
- collapsing the plurality of augmented bands to generate an augmented image;
- generating the ECG filtered augmented image based on the augmented image and the electrical activity; and
- displaying the ECG filtered augmented image on a display.

14. The method of claim 13, further comprising isolating at least one frequency band from the plurality of frequency bands.

15. The method of claim 14, further comprising amplifying the temporally filtered bands, before adding each band in the plurality of frequency bands to a corresponding band in the plurality of temporally filtered bands, to generate a plurality of augmented bands.

16. The method of claim 13, further comprising generating a baseline time varying amplified color.

17. The method of claim 16, further comprising:
averaging the baseline time varying amplified color; and
removing the averaged baseline time varying amplified color from the augmented image to generate the ECG filtered augmented image.

18. The method of claim 13, further comprising emitting light onto the target tissue having a wavelength that selectively is absorbed or reflected by arterial blood.

19. The method of claim 13, further comprising emitting light onto the target tissue having a wavelength that selectively is absorbed or reflected by venous blood.

20. The method of claim 13, further comprising applying a temperature filter to the region of interest of the patient to identify heat signatures of abnormal tissue.

* * * * *